(12) United States Patent
Chen et al.

(10) Patent No.: US 9,216,003 B1
(45) Date of Patent: Dec. 22, 2015

(54) UNIVERSAL INTRAORAL DIGITAL SENSOR HOLDER FOR EXISTING DIGITAL SENSOR SYSTEMS IN DENTISTRY

(71) Applicant: Cyber Medical Imaging, Inc., Los Angeles, CA (US)

(72) Inventors: Adam Chen, Pacific Palisades, CA (US); Douglas C Yoon, Beverly Hills, CA (US)

(73) Assignee: CYBER MEDICAL IMAGING, INC., Los Angeles, CA (US)

(*) Notice: Subject to any disclaimer, the term of this patent is extended or adjusted under 35 U.S.C. 154(b) by 58 days.

(21) Appl. No.: 13/943,548

(22) Filed: Jul. 16, 2013

Related U.S. Application Data

(60) Provisional application No. 61/671,974, filed on Jul. 16, 2012.

(51) Int. Cl.
*A61B 6/14* (2006.01)
*A61C 19/04* (2006.01)

(52) U.S. Cl.
CPC . *A61B 6/145* (2013.01); *A61B 6/14* (2013.01); *A61C 19/04* (2013.01)

(58) Field of Classification Search
CPC .......... A61C 19/00; A61C 19/04; A61C 1/08; A61C 1/082; A61C 1/084; A61C 1/088; A61C 3/00; A61B 6/14; A61B 6/145; G03B 42/04; G03B 42/042

USPC .......... 378/38, 167, 168, 177, 189–191, 204, 378/208, 210; 433/29, 215, 229
See application file for complete search history.

(56) References Cited

U.S. PATENT DOCUMENTS

| | | | | |
|---|---|---|---|---|
| 5,119,410 A | * | 6/1992 | Donato | 378/170 |
| 5,737,388 A | * | 4/1998 | Kossila | 378/168 |
| 6,461,038 B2 | * | 10/2002 | Pellegrini et al. | 378/191 |
| 2005/0220272 A1 | * | 10/2005 | Glazer | 378/168 |
| 2009/0141866 A1 | | 6/2009 | Fenske et al. | |
| 2009/0168969 A1 | * | 7/2009 | Schmulenson et al. | 378/170 |

* cited by examiner

*Primary Examiner* — Anastasia Midkiff
(74) *Attorney, Agent, or Firm* — Roy L. Anderson

(57) ABSTRACT

A universal dental digital sensor holder has a bite block connected to a rod that has a connector which is used to flexibly attach a sensor holder so as to allow rotational movement of the sensor relative to the bite block and multiple sensor holders are removably connected to the connector so that they can be used to obtain different radiographic projection views due to their differing configurations for holding the intraoral sensor in the patient's mouth. The bite block can have an opening formed in it fitted with a sleeve to allow access to a tooth located beneath the opening in the patient's mouth. A cable protector can be formed in the rod adjacent an anterior bite surface so that an intraoral sensor cable can be held adjacent the rod and at least partially protected from one or more teeth biting the anterior bite surface.

15 Claims, 7 Drawing Sheets

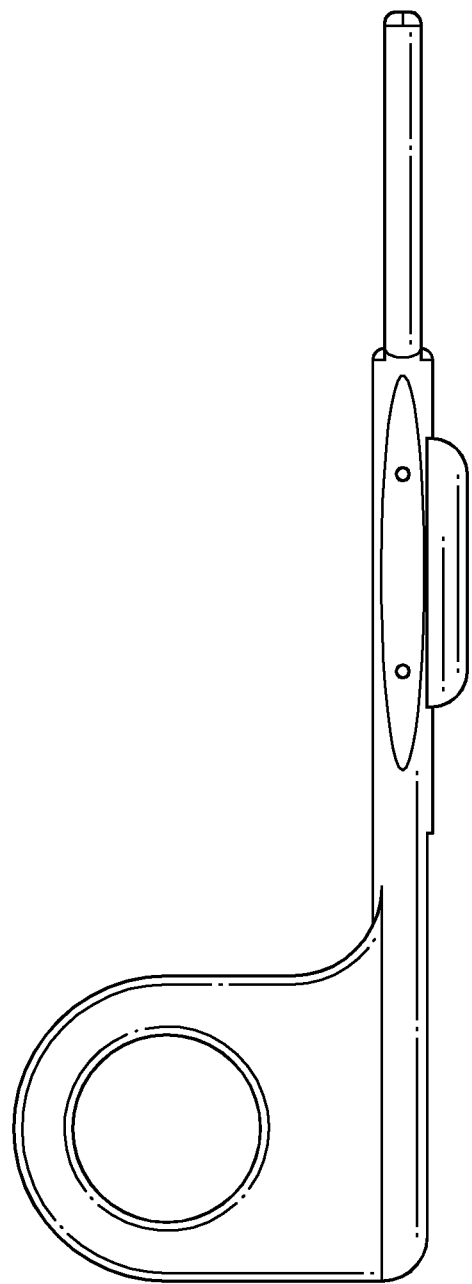 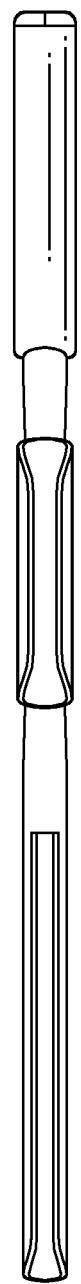
FIG. 2
FIG. 3

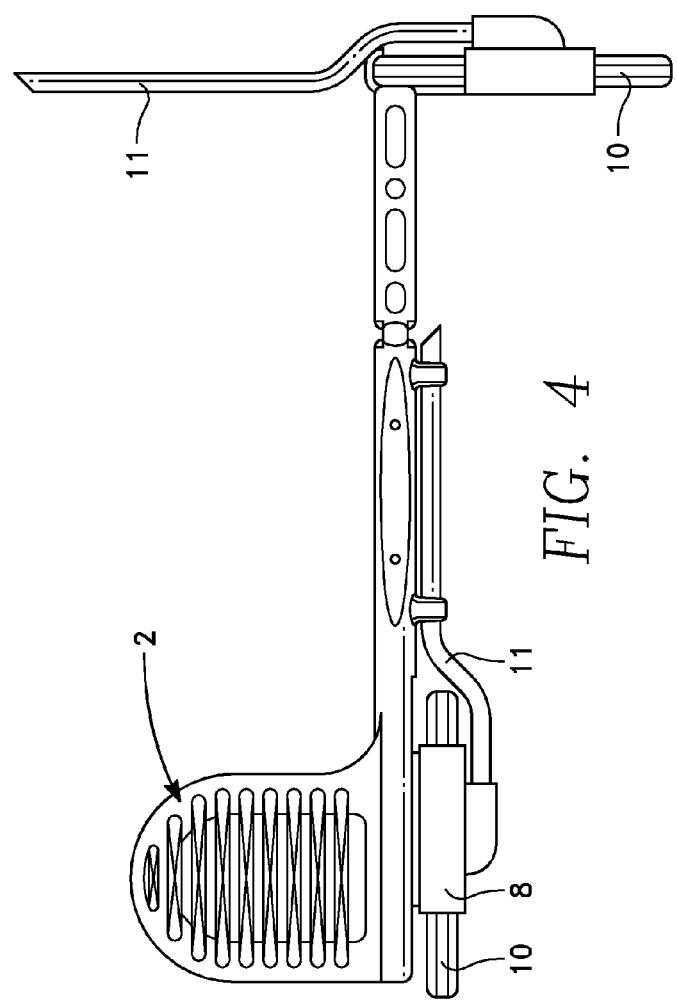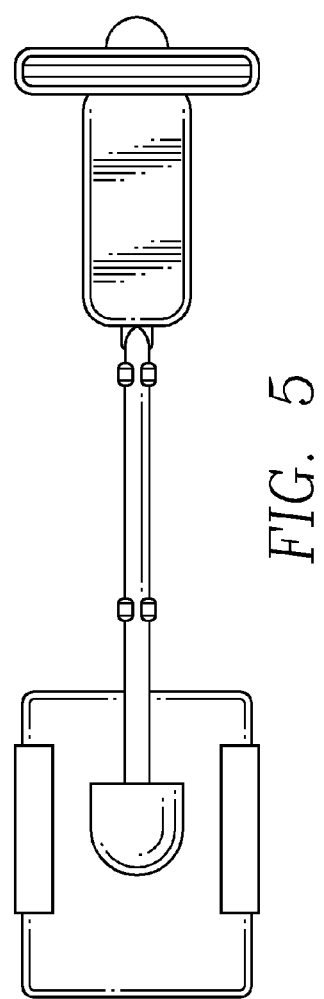

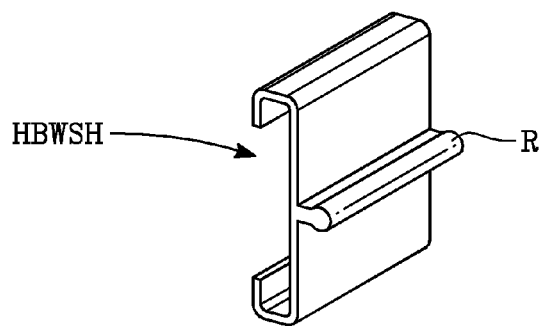
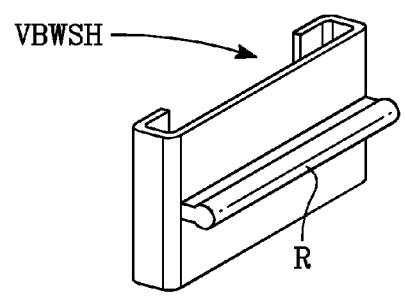
FIG. 8A  FIG. 8B
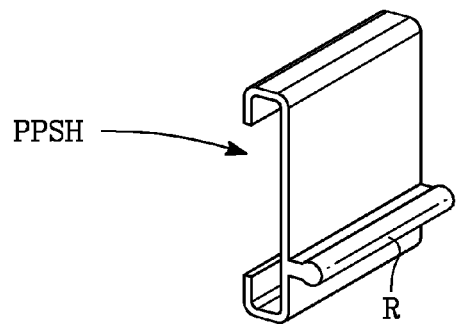
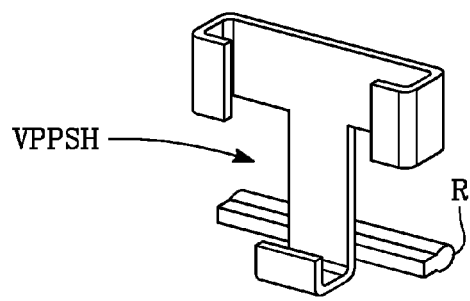
FIG. 8C  FIG. 8D

UNIVERSAL INTRAORAL DIGITAL SENSOR HOLDER FOR EXISTING DIGITAL SENSOR SYSTEMS IN DENTISTRY

CROSS-REFERENCE TO RELATED APPLICATIONS

This application is a non-provisional of U.S. Ser. No. 61/671,974, filed Jul. 16, 2012, the disclosure of which is specifically incorporated herein by reference.

FIELD OF THE INVENTION

The field of the present invention is dentistry and, specifically, devices used by dentists when working with a dental intraoral digital sensor in a patient's mouth for taking intraoral radiographs.

BACKGROUND OF THE INVENTION

Dental intraoral digital sensors have been in used in dentistry for the last two decades; their popularity is gaining and will eventually replace x-ray film as the imaging medium of choice for the dental profession. The intraoral digital sensors have mainly been used to capture digital radiographic images of teeth, gum, and bone allowing the dental practitioner to communicate clinical findings to the patient via computer software that can capture and display the image. Like the traditional intraoral dental X-ray film packet, intraoral dental digital sensors are placed in the patient's mouth with digital sensor holders of similar designs to produce the same geometry used in dental film radiography techniques. Therefore, currently, the available intraoral digital sensor holders have evolved directly from intraoral dental X-ray film packet holders of the past, and most have retained the identical components of the X-ray film holder with only minor dimensional changes and adaptations to secure an intraoral digital sensor instead of intraoral X-ray film with little thought to the major physical differences between the intraoral X-ray film and intraoral digital sensor.

There are significant physical differences between the typical intraoral digital sensor versus the traditional intraoral X-ray film packet. The intraoral X-ray film packet has a thickness of about one to two millimeters, and is relatively flexible and soft versus the thicker and completely rigid intraoral digital sensor. The intraoral digital sensor is much thicker than the X-ray film packet, having a thickness of four to eight millimeters, it is also rigid, attached to a long flexible cord to interface with the computer. Because of these intrinsic physical differences, the traditional universal X-ray film holding device tends to be a relatively thick (4-5 mm) rigid device because the jaws of the X-ray film holder must clamp and holdfast a thin, often wet flexible piece of X-ray film in place during use. The flexible X-ray film packet is soft and pliable when placed in the patient's oral cavity and is generally more tolerable for most patients in terms of comfort. However, because the intraoral digital sensor is much ticker and rigid compared to the X-ray film, the exact opposite qualities of thinness and flexibility is desired in an intraoral digital sensor holder in respect to maximizing patient comfort. Therefore, there are deficiencies in the current designs of existing universal digital sensor holders or systems with respect to maximizing patient comfort during use and, also as a class, current designs lack any physical protection to keep the digital sensor cable from being damaged due to the patient's teeth biting on the sensor cable. Current data show that damage to the digital sensor cable accounts for about ninety percent of the damage suffered by dental digital sensors during normal use. The cost of replacing the damaged digital sensor cable can be several hundred to several thousand dollars.

Another issue the user of the rigid intra-oral digital sensor often encounters is patient discomfort due to the impingement of the hard rigid sensor against the sensitive soft tissues of the patient. This problem is further exacerbated by an inflexible rigid sensor holder.

SUMMARY OF THE INVENTION

The present invention is generally directed to a universal dental digital sensor holder that can be used to obtain intraoral radiographic images from an intraoral sensor useful in providing radiographic projection views of a patient's mouth. The universal holder has a bite block that is connected to an elongate support structure (such as a rod) that has a connector which is used to flexibly attach a sensor holder so as to allow rotational movement of the sensor relative to the bite block and multiple sensor holders are removably connected to the connector so that they can be used to obtain different radiographic projection views due to their differing configurations for holding the intraoral sensor in the patient's mouth.

The universal dental digital sensor holder can also be used with a bite block that has an opening formed in it fitted with a sleeve to allow access to a tooth located beneath the opening in the patient's mouth.

The universal dental digital sensor holder can use a connector which is either a groove or a raised area that can be inserted into the groove to form a tongue-and-groove connection, it being especially preferred that the groove is located in the main body while each of the removable multiple sensor holders has a raised area to fit into such groove. The easy removability of such sensor holders allows the sensor holders to be designed to accommodate differing anatomical considerations that arise in obtaining different radiographic projection views of a patient's mouth, so sensor holders can be designed so as to provide an anterior and posterior periapical view sensor holder, a horizontal bitewing view sensor holder and a vertical bitewing sensor holder, all of which can be fitted with a raised area for use in a tongue-and-grove connection.

The elongate support structure can also have an anterior bite surface integrally formed in it and an anterior periapical view sensor holder can be connected to the elongate support structure at the opposite end from the bite block. A cable protector can be integrally formed into the elongate support structure adjacent the anterior bite surface so that a cable extending from the intraoral sensor can be inserted into the cable protector to thereby hold the cable adjacent the elongate support structure and at least partially protect the cable from one or more teeth in the patient's mouth that bite the anterior bite surface.

Accordingly, it is an object of the present invention to provide for the specific applications of intra operative radiographs during endodontic treatment and implant placement.

It is a further object of the present invention to provide for the protection of the dental digital sensor cable and management of the digital sensor cable when used with intra oral dental digital sensor.

Another object of the present invention is to provide for a sensor holder that will allow the vertical rigid sensor to pivot at the junction of the horizontal bite block, thereby reducing the pressure placed on the sensitive soft tissue on the patient's maxillary palate or lingual aspect of the mandible when the patient bites down on the bite block.

These and further objects and advantages will be apparent to those skilled in the art in connection with the drawings and the detailed description of the invention set forth below.

DETAILED DESCRIPTION OF THE DRAWINGS

FIG. 1 is an isometric view that illustrates the universal digital sensor holder of the present invention with a sensor cable protector while FIG. 2 is a top view and FIG. 3 is a side view of the sensor cable protector and the slot for the sensor holder of FIG. 1.

FIG. 4 is a top view that illustrates the universal digital sensor holder of the present invention without a cable protector, FIG. 5 is its side view.

FIG. 8A is a side view of a horizontal bitewing sensor holder, FIG. 8B is a side view of a vertical bitewing sensor holder, FIG. 8C is a side view of a posterior periapical sensor holder, and FIG. 8D illustrates a vertical posterior periapical sensor holder, all of which can be used as sensor holder 8 in a universal digital holder of the present invention.

DETAILED DESCRIPTION OF THE INVENTION

Figure 1:
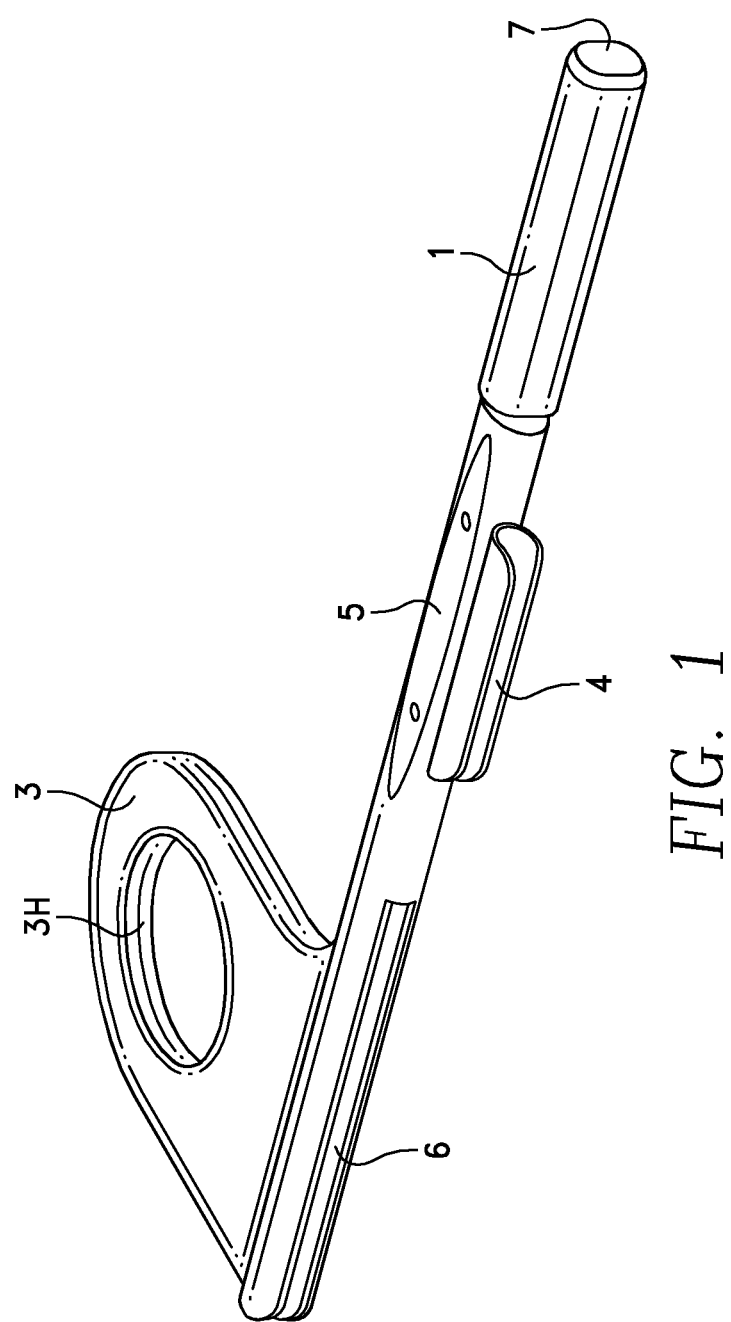

The present invention is generally directed to a universal dental digital sensor holder with protective sensor cable holder and cover, which can be of minimally intrusive and maximally flexible in design, utilizing a combination of materials which solves the problem of patient discomfort and digital sensor cable damage during intra oral radiographic exams. The use of this dental digital sensor holder with a protective digital sensor cable cover will protect the dental digital sensor from damage caused by patients biting directly on the sensor cable during use leading to premature failure.

The present invention seeks to minimize patient discomfort when taking intra oral dental radiographs with a dental intraoral digital sensor while allowing the dental professional to take the various diagnostic radiographic views: anterior periapical projection, posterior periapical projection, horizontal bitewing projection, vertical bitewing projection with a single universal digital sensor holding device.

The universal digital sensor holder may be a composite of plastics with differing characteristics like overmoldings made of a softer plastic having the consistency of smooth rubber covering the harder plastic in specific areas located on the outside surface of the holder. This universal dental digital sensor holder is able to secure a wide variety of shapes and sizes of commercially available digital dental x-ray sensors and is designed to be minimally intrusive by having a minimal physical size envelope—all of its parts should preferably be made as thin as possible. The overall smooth rounded shapes and contours of the sensor holder are designed to follow the general external contours of the digital sensor while using minimal thickness of material to avoid any added external bulk to the digital sensor and digital sensor holder assembly. With all of the material of the various parts, it is especially preferred that there be a transition from the thickest to the thinnest regions as the part moves towards its ends so as to have as gradual a change in thickness as possible. In addition, the use of specially designed internal male female connectors between the specific parts at the connection points further reduce any external bulk; these connecting devices will also use existing physical space that is part of the sensor holder.

Due to the intrinsic inflexibility of the dental digital sensor, any additional bulk will cause patient discomfort especially while taking periapical views of the maxillary molar area. The minimal thickness of the sensor holder material will also minimize the radiographic shadow it will generate in the captured image. This universal digital sensor holder's specially designed internal male female connector is also designed to allow some rotational flexibility between the dental digital sensor and the holder from the male/female joint and or material deformation, allowing the sensor to rotate slightly in the coronal plane of the patient to lessen the discomfort caused by the thick rigid dental digital sensor impingement of the sensitive oral tissue to address this common problem.

It is especially preferred that all corners and edges should have as large a radius as possible to distribute the pressure on a larger area thereby ensuring more comfort when any portion of the digital sensor holder comes into contact with the patient's sensitive oral tissues. The construction of this universal digital sensor holder may be a composite of plastics with differing characteristics like overmoldings made of a softer elastomeric plastic having the consistency of smooth silicone rubber covering the harder plastic in specific areas located on the outside surface of the holder to further increase patient comfort during use.

The single digital sensor holder of the present invention will allow the dental professional to take the various anterior, posterior, and bitewing views that comprise of a complete dental radiographic exam series. In addition, a special version of this universal digital sensor holder will also allow the dental professional to take radiographs during endodontic treatment and dental implant placement procedures. A round opening on the bite block of the holder will hold a removable or integral round cylindrical ring which will allow for the placement of endodontic files into the treatment tooth when the radiograph is taken with the intraoral digital sensor. The same device will also allow the user to take a digital radiograph intra-operatively with a pilot drill or pilot guide posts during dental implant placement procedures.

The present invention also provides an integral digital sensor cable holder and protective cover that will protect the sensor cable from damage due to the patient's teeth biting on the sensor cable. This integral digital sensor cable holder and protective cover design concept can also be made as a separate independent unit that can be retrofitted to existing sensor holder devices having common physical characteristics.

One aspect of this invention deals with the protection of the digital sensor cable from damage due to the patient's teeth biting on the sensor holder or bite block. It is comprised of two major parts, the bite block/handle assembly and removable sensor holder modules. The bite block/handle assembly incorporates an integral digital sensor cable holder/protector. This digital sensor holder cable holder/protector are located where the patient's teeth will contact the digital sensor cable where it exits the patient's mouth on the digital sensor holder. This will allow the user to firmly attach the digital sensor cable to the handle of the digital sensor holder protecting the digital sensor cable at the point where the patient's teeth will usually come into contact with the digital sensor cable. The digital sensor holder cable holder/protector's semi-rigid outer structure will resist compression of the digital sensor cable and prevent damage to the very thin gauged wires within the digital sensor cable. This digital sensor holder's cable holder/protector can also reduce the direct tension placed at the junction of the sensor cable and sensor shell—an area which is know to cause cable damage issues. The secured digital sensor cable by the sensor cable holder/protector will allow the user to have a very predicable and neat management of the digital sensor cable securely in place and out of the way and preventing damage to the cable from biting forces during a dental radiographic exam.

The design of the fixed digital sensor cable holder and protective cover can be a round hollow "C" shaped tube, open on one side with a continuous diameter matching the requirements of the dental digital sensor cable diameter with a slightly enlarged flared conical shaped ends to ease of insertion or removal of the digital sensor cable. The outside shape of the "C" shaped tube can be rounded and flared to match the specific dimensions or design of the sensor holder component.

One example of a method to secure this attachment to the existing digital sensor holder or systems like the Rinn Dentsply XCP is the use of round pins with the same diameter and spacing as the pins on the metal or plastic rods which attaches to the sensor holder bite block, allowing it to be secured to either side of the sensor holder bite block that is unused by the sensor holder assembly.

The present invention will now be described in greater detail and by reference to the Figures which illustrate some preferred embodiments of the present invention. In the Figures and the following description, designations indicate various features of the invention, with like designations referring to like features throughout both the drawings and the description. The following is a glossary of the elements identified in the Figures.

Figure 1A:
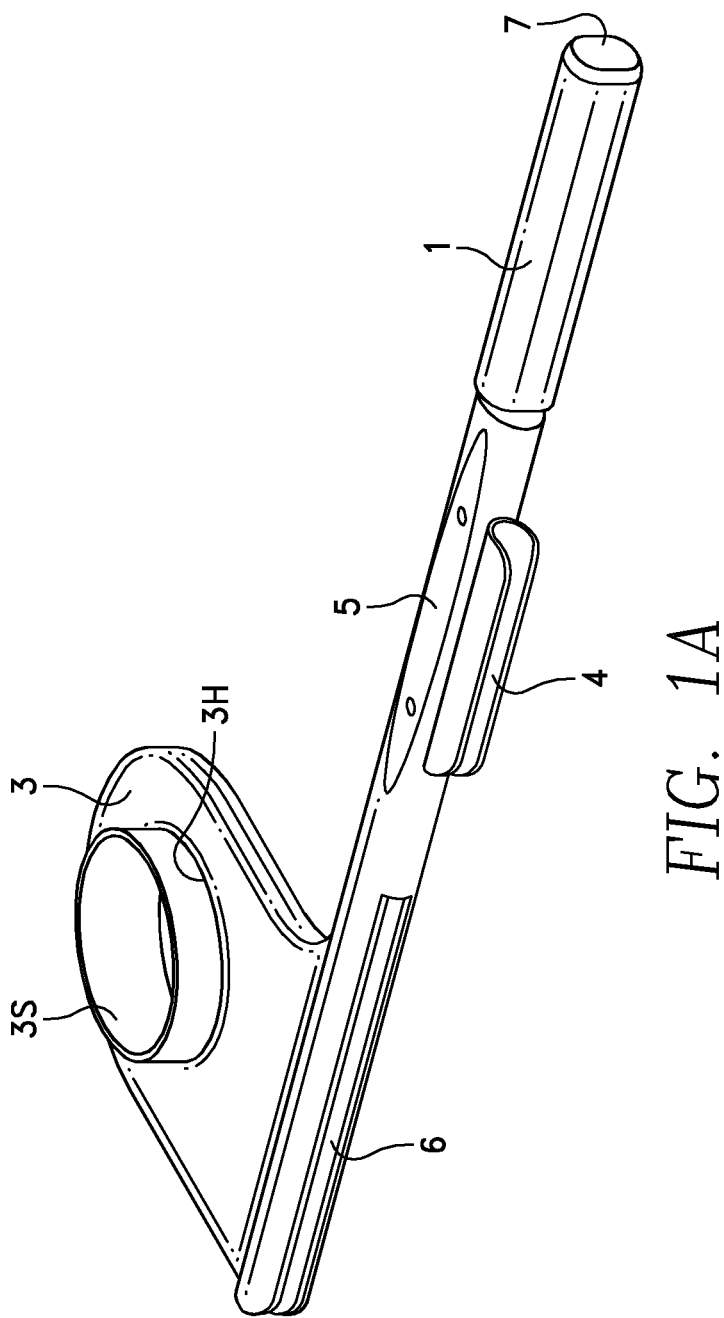
FIG. 1A illustrates an endodontic file/spacer sleeve inserted into the device of FIG. 1.

GLOSSARY 1 rod
2 bite block
3 bite block for endodontic application
3H opening for endodontic application
3S endodontic file/spacer sleeve that fits into opening 3H
4 sensor cable protector
4CH sensor cable holder
5 anterior bite surface
6 slot for sensor holder
7 end for inserting into anterior sensor holder
8 sensor holder
8E sensor extension
9 anterior sensor holder
10 digital sensor
11 digital sensor cable
12 rods for retrofit existing devices
13 female groove
R ridge formed in a sensor holder for insertion into a female groove 13
HBWSH horizontal bitewing sensor holder
PPSH posterior periapical sensor holder
VBWSH vertical bitewing sensor holder
VPPSH posterior periapical sensor holder FIG. 1 illustrates a preferred embodiment of the present invention that is useful in endodontic applications. In this embodiment, bite block 3 has an opening 3H that can be used to fit a cylinder sleeve 3S (see FIG. 1A where the sleeve is fitted into opening 3H) used for allowing the handles of endodontic files to protrude from a tooth undergoing an endodontic procedure. Note that FIG. 4 illustrates a similar embodiment, except that its bite block 2 is not designed with an opening, and it is not specially designed for use in endodontic applications.

Figure 6:
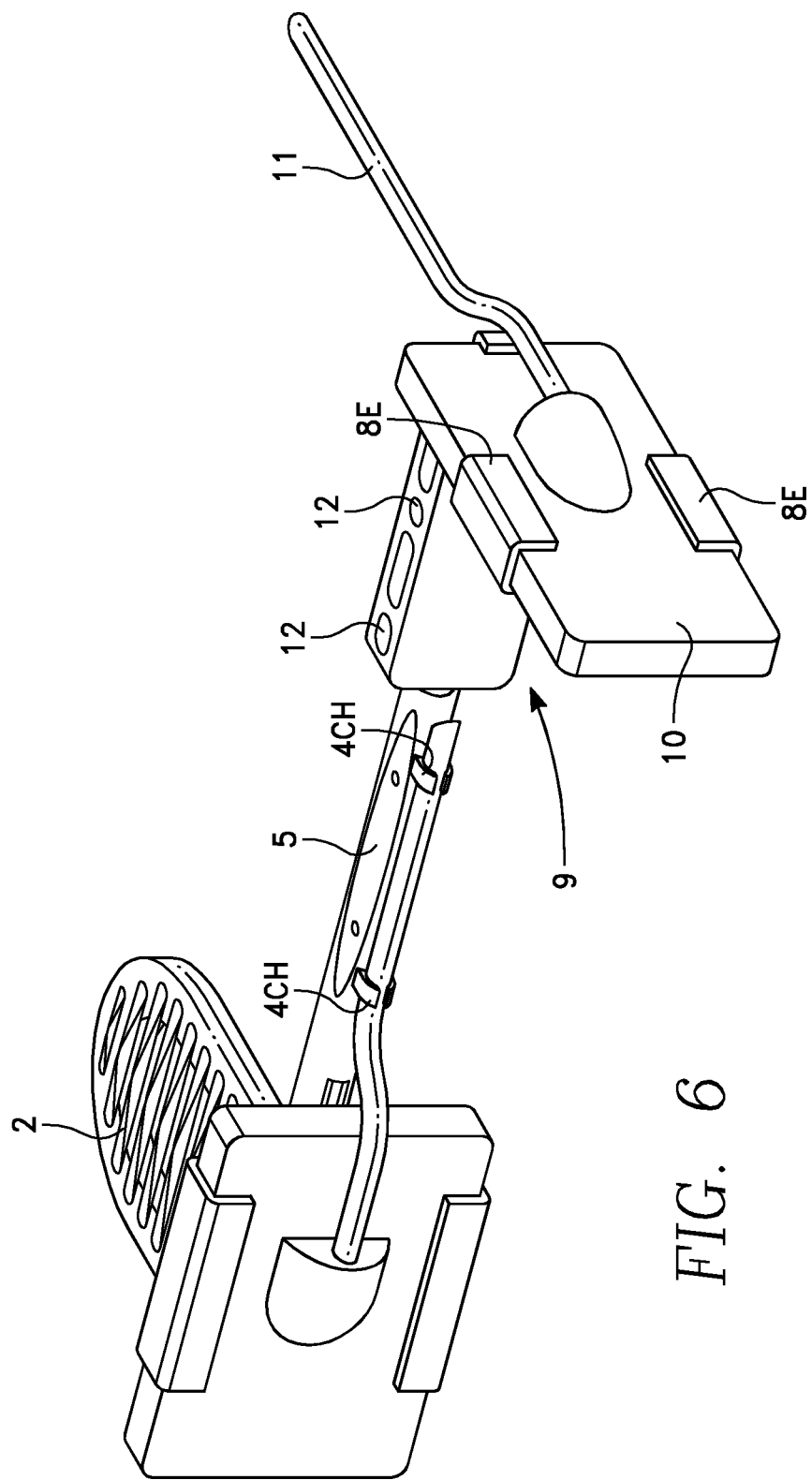
FIG. 6 is its isometric view and FIG. 7 is its end view—this end view shows the unique oval attachment design that can be incorporated into existing sensor holder bite blocks to make it compatible with this unique holder.

It is especially preferred that the universal holder of the present invention has an elongate support structure that is shaped in the form of a rod, and the Figures of the present invention illustrate one preferred form of such a rod. Rod 1 has end 7 for inserting into an anterior sensor holder 9 (as is shown in FIG. 6). Rod 1 has an anterior bite surface 5 and, immediately adjacent and contiguous with bite surface 5 (see FIG. 1), sensor cord protector 4 serves to protect sensor cable 11 when inserted into a patient's mouth. Note that the embodiment shown in FIG. 4 does not have a sensor cable protector 4, but it does have a cable holder 4CH which helps manage a sensor cable and hold it next to rod 1. Sensor cable protector 4 can be formed integrally with rod 1 (as shown in FIG. 1) or it can be used as an add-on accessory or retrofit for use in existing dental devices where an intraoral digital sensor maybe deployed. When a sensor cable protector is used as an add-on accessory or retrofit, it can have two rods (now shown) that can be fitted into existing sensor holder rod holes 12 such as those shown as FIG. 6.

Rod 1 has slot 6 for mating with groove 13 of sensor holder 8. Slot 6 and groove 13 serve as a male/female connection which can also be described as forming a tongue-and-groove connection and their placement can be reversed so that rod 1 has a groove and sensor holder 8 has a slot. Also, other alternative attachment/detachment mechanisms can be used to connect/disconnect sensor holder 8 to rod 1, although the tongue-and-groove connection shown in the Figures is especially preferred in view of its sleekness and ease of use.

It should also be noted that the tongue-and-groove connection can readily be adapted, according to design considerations, to allow for rotational movement of sensor 10 relative to bite block 2, and such rotational movement helps promote patient comfort in use. While more rotation helps promote patient comfort, it also introduces a length distortion into intraoral radiographic images obtained from an intraoral sensor that is not perpendicular to the bite plane, but such additional length distortion should be an acceptable trade off for patient comfort provided the amount of additional length distortion is not too significant so as to interfere with a dental professional's use of the intraoral radiographic images obtained. For example, a sensor rotation of 25 degrees from perpendicular to the bite plane will introduce an additional length distortion of less than 10%, but such additional length distortion should not be too significant so as to interfere with a dental professional's use of the intraoral radiographic images obtained, so allowing such rotational movement helps promote patient comfort and is especially preferred. (The bite plane is in reference to the dental anatomic description of an occlusal plane where the upper and lower teeth meet.)

Figure 7:
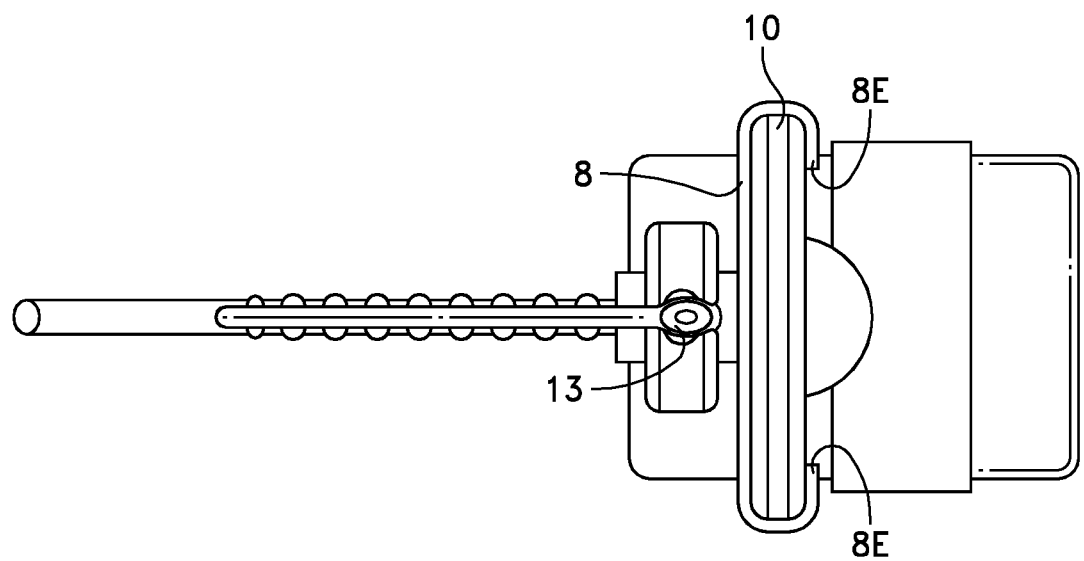

Sensor holder 8 is shown in FIG. 7 as having extensions 8E that form a "C" shape into and out of which sensor 10 can be inserted. Sensor holder 8 could also be closed around sensor 10, or use an elastic closure/holding mechanism for holding sensor 10 in sensor holder 8.

The design of sensor holder 8 can be varied to accommodate anatomical considerations that come into play when a dental professional wants to obtain different radiographic projection views of a patient's mouth, and FIGS. 8A-8D illustrate differing sensor designs based upon what radiographic projection view is sought. Thus, FIG. 8A illustrates a side view of a horizontal bitewing sensor holder, HBWSH, which is shown as the left sensor holder in FIG. 6. In this configuration sensor 10 is held horizontally relative to rod 1 and the ridge R that fits into groove 13 of rod 1 is in the middle of the sensor holder. FIG. 8B illustrates a vertical bitewing sensor holder, VBWSH, in which sensor 10 is now rotated ninety degrees relative to FIG. 8A, with ridge R remaining in the center of the holder. A third sensor holder which will fit in the same groove 13 will have sensor 10 horizontal to the rod, as was the case in FIG. 8A, but now ridge R is moved off center to create a posterior periapical view sensor holder PPSH. FIG. 8D illustrates a posterior periapical sensor holder which has the same arms found in FIGS. 8A-C to hold sensor 10, but then it also has an extra length which is added to such arms, the long part of a T shape, and at the bottom of this extra section ridge R is added for fitting into the same groove 13.

Based upon the above description, it should now be readily apparent to a dental professional that the present invention provides a universal dental digital sensor holder that is easy to use and which can be used to obtain any desired radiographic projection view of a patient's mouth. The various sensor holders that can be used to obtain different radiographic projection views of a patient's mouth can be sold separately or as part of a complete kit.

While the invention has been described herein with reference to certain preferred embodiments, those embodiments have been presented by way of example only, and not to limit the scope of the invention. Additional embodiments thereof will be obvious to those skilled in the art having the benefit of this detailed description.

Accordingly, it will be apparent to those skilled in the art that still further changes and modifications in the actual concepts described herein can readily be made without departing from the spirit and scope of the disclosed inventions.

What is claimed is:

1. An apparatus for obtaining an intraoral radiographic image from an intraoral sensor useful in providing a radiographic projection view of teeth in a patient's mouth, comprising:
    a rod having a first end and a second end;
    a bite block integrally formed with, and non-detachable from, the first end of the rod, said bite block and said first end of the rod lying in a first fixed plane so that the bite block cannot rotate outside of said first fixed plane;
    a groove formed in the rod beginning at the first end and extending along the rod opposite the bite block, wherein the first fixed plane intersects the groove; and
    a cable protector integrally formed in the rod adjacent the anterior bite surface;
    wherein the apparatus can be used to obtain the intraoral radiographic image when a sensor holder holding the intraoral sensor is connected to the rod by inserting a raised area of the sensor holder into the groove so that the sensor holder will lie in a second fixed plane that is perpendicular to the first fixed plane; and
    wherein a cable extending from the intraoral sensor can be inserted into the cable protector to thereby hold the cable adjacent the rod and at least partially protect the cable from one or more teeth in the patient's mouth that bite the anterior bite surface.

2. The apparatus of claim 1, further comprising an opening formed in the bite block to allow access to a tooth located beneath an opening in the patient's mouth.

3. The apparatus of claim 2, further comprising a sleeve attached to the bite block so that it is fitted to the opening and extends away from the tooth located beneath the opening in the patient's mouth.

4. The apparatus of claim 1, further comprising a first sensor holder uniquely suited for obtaining the radiographic projection view from the intraoral sensor.

5. The apparatus of claim 4, wherein the first sensor holder is a posterior periapical view sensor holder.

6. The apparatus of claim 4, wherein the raised area of the first sensor holder and the groove allow slight rotational movement of the sensor relative to the bite block.

7. The apparatus of claim 1, further comprising an anterior periapical view sensor holder connected to the rod at the second end, wherein the anterior periapical view sensor holder will hold the intraoral sensor so that it lies in a third fixed plane that is perpendicular to both the first fixed plane and the second fixed plane.

8. A method for obtaining a radiographic projection view of teeth in a patient's mouth, comprising:
    inserting an intraoral sensor having a cable into a sensor holder having a raised area;
    inserting the raised area into a groove extending from a first end of a rod, said rod having a bite block and a cable protector connected to the rod adjacent the anterior bite surface, said bite block being fixedly attached to the rod so that the first end of the rod and the bite block lie in a first fixed plane so that the bite block cannot rotate outside of said first fixed plane, said intraoral sensor being held in said sensor holder so that it lies in a second fixed plane that is perpendicular to the first fixed plane;
    inserting the cable into the cable protector;
    inserting the intraoral sensor connected to the rod into the patient's mouth and obtaining a radiographic image while the intraoral sensor is inside of the patient's mouth;
    using the radiographic projection to obtain the radiographic image,
    removing the intraoral sensor connected to the rod from the patient's mouth;
    removing the intraoral sensor from the sensor holder;
    connecting a second sensor holder to the rod;
    inserting the intraoral sensor connected to the rod and the second sensor holder into the patient's mouth and obtaining a second radiographic image while the intraoral sensor is inside of the patient's mouth; and
    using the second radiographic projection to obtain a second radiographic image.

9. The method of claim 8, wherein the second sensor holder is connected to the rod by inserting a second raised area of the second sensor holder into the groove and wherein the sensor holder and the second sensor holder are different from each other and selected from the group consisting of a posterior periapical sensor holder, a posterior horizontal bitewing sensor holder and a posterior vertical bitewing sensor holder.

10. The method of claim 8, wherein the second sensor holder is an anterior periapical sensor holder connected to the second end and the sensor holder is selected from the group consisting of an anterior periapical sensor holder and an anterior bitewing sensor holder.

11. The apparatus of claim 4, wherein the first sensor holder is a posterior horizontal bitewing view sensor holder.

12. The apparatus of claim 4, wherein the first sensor holder is a posterior vertical bitewing sensor holder.

13. An apparatus for obtaining a plurality of intraoral radiographic images from an intraoral sensor useful in providing a radiographic projection view of teeth in a patient's mouth, comprising:
    a rod having a first and a second end;
    a bite block fixedly attached proximate the first end, said bite block and said first end of the rod lying in a first fixed plane so that the bite block cannot rotate outside of said first fixed plane;
    a groove formed in the rod beginning at the first end and extending along the rod;
    a plurality of sensor holders, each of which is capable of holding the intraoral sensor, each of which is uniquely suited for obtaining a unique view selected from the group consisting of a posterior periapical view, a posterior horizontal bitewing view and a posterior vertical bitewing view, each of which can be connected to the rod by inserting a raised area into the groove so that the intraoral sensor is held in a second fixed plane that intersects with the first fixed plane.

14. The apparatus of claim 13, further comprising an anterior periapical sensor holder connected to the second end of the rod capable of holding the intraoral sensor in a third fixed plane that intersects with both the first fixed plane and the second fixed plane.

15. The apparatus of claim 14, wherein the plurality of sensor holders is comprised of three sensor holders.

* * * * *